United States Patent [19]

Tarbutton

[11] 4,215,197

[45] Jul. 29, 1980

[54] TEST MEANS AND METHOD FOR CREATININE DETERMINATION

[75] Inventor: Peter N. Tarbutton, Houston, Tex.

[73] Assignee: Miles Laboratories, Inc., Elkhart, Ind.

[21] Appl. No.: 931,030

[22] Filed: Aug. 4, 1978
(Under 37 CFR 1.47)

[51] Int. Cl.$^2$ ............................................. G01N 31/14
[52] U.S. Cl. ......................................... 435/18; 435/26
[58] Field of Search .......................... 195/103.5 R, 99; 435/18, 26

[56] References Cited

U.S. PATENT DOCUMENTS

| | | | |
|---|---|---|---|
| 3,867,259 | 2/1975 | Forgione | 195/103.5 R |
| 3,907,644 | 9/1975 | Möllering et al. | 195/103.5 R |
| 3,912,588 | 10/1975 | Möllering et al. | 195/103.5 R |
| 3,929,580 | 12/1975 | Forgione et al. | 195/99 |
| 4,012,286 | 3/1977 | Sanderson et al. | 195/103.5 R |

*Primary Examiner*—Esther M. Kepplinger
*Attorney, Agent, or Firm*—Charles J. Herron

[57] ABSTRACT

Test means, such as a composition or a test device incorporating the composition, method of making the test device and process for determination of creatinine using the test means are disclosed. More particularly, creatinine is measured by incubating with a test means, such as a composition, comprising a creatinine hydrolyzing enzyme, creatine amidinohydrolase, sarcosine dehydrogenase and a tetrazolium indicator and observing any resultant color change. A colored formazan is produced in proportion to the creatinine present. The sensitivity of the system is increased and the detection limit lowered by including formaldehyde dehydrogenase, diaphorase and nicotinamide adenine dinucleotide (NAD). Creatine or sarcosine are measured in this system by omitting the creatinine hydrolyzing enzyme or the creatinine hydrolyzing enzyme and the creatine amidinohydrolase, respectively, from the composition used in testing for creatinine. The enzymes, tetrazolium indicator and other components are compatible and may be combined in a single solution. The compositions are advantageously incorporated with a carrier, such as a matrix or tablet, to provide a test device.

28 Claims, 1 Drawing Figure

TEST MEANS AND METHOD FOR CREATININE DETERMINATION

BACKGROUND OF THE INVENTION

The present invention relates generally to the field of diagnostic test compositions, and more particularly, to diagnostic tests useful for determination of creatinine and enzymatic products thereof.

Creatinine is a product of the endogenous metabolism of muscle. The amount of creatinine in the urine reflects total muscle mass and the degree of muscular activity. It is unrelated to dietary protein ingestion. It arises primarily from creatine and phosphocreatine during energyliberating processes in various body tissues, primarily muscle tissue.

The amount of creatinine in the urine of each individual is remarkably constant and varies little from day to day. Measurement of urinary creatinine may be used to determine the accuracy of 24-hour urine collections. Normal creatinine excretion ranges from 0.6 to 1.5 grams (g)/day in women and from 1.0 to 2.0 (g)/day for men. Creatine is almost completely reabsorbed by the renal tubules so that only a small amount, less than 100 milligrams (mg)/24 hours, is found in the urine. Therefore a principal value for the determination of creatinine is as a urine marker. In the majority of clinical conditions where urinalysis is part of a diagnostic profile, the creatinine level remains constant and there is an indicator of the volume and concentration or urine output in such patients.

Urinary creatine is elevated in the early stages of muscular dystrophy, when muscle destruction is occurring rapidly, and in any wasting disease involving increased tissue catabolism. It is elevated during severe and strenuous muscular activity and in hyperthyroidism. Urinary creatinine is decreased during the later stages of muscular dystrophy and whenever renal function is impaired. Urinary creatine increases in the same disease states that produce an increase in urinary creatinine.

The most widely known method for the determination of creatinine is the non-enzymatic Jaffe method which involves the formation of an orange-red color with an alkaline picrate solution. This method is not specific for creatinine, however, since many pseudocreatinine substances also react with alkaline picrate. Various attempts at improvement on the Jaffe method are discussed in Henry, *Clinical Chemistry*, at pages 541 et seq and in Dewhurst, U.S. Pat. No. 3,705,013. All are based on non-enzymatic color development for quantification of creatinine.

Many workers have sought a source of enzymes useful in creatinine determinations. Creatine and its anhydride, creatinine, do not occur in bacteria, yeast or molds. However, over forty different strains of bacteria and yeast have been shown to be capable of utilizing creatine and creatinine. The literature discloses the existence of at least four different enzymatic pathways whereby bacteria and molds may metabolize creatinine.

Appropriate soluble enzymes have therefore been sought which could catalyze specific, measurable reactions of creatinine. Among others, creatinase, creatininase, and a glycocyaminase have been characterized. An enzyme referred to as creatine-mutase has been isolated from soil bacteria and is responsible for the equilibrium adjustment between creatinine and creatine.

Mollering U.S. Pat. No. 3,806,416 discloses two enzymes referred to as creatinine amidohydrolase and creatine amidinohydrolase prepared from Alcaligenes spec. WS 51400 and Pencillium WS 90001. The former enzyme is disclosed to convert creatinine to creatine, and the latter, creatine to sarcosine plus urea. Holz Pat. No. 3,806,420 discloses a method for producing these enzymes from these strains.

Mollering U.S. Pat. No. 3,907,644 discloses a creatinine detection method wherein an aqueous creatinine-containing solution is incubated with creatinine amidohydrolase at a pH between 7.5 and 9 and either the creatine formed or the decrease of creatine is determined in known manner. Additionally, use of creatinase, also classified as creatine amidinohydrolase by the reference, to convert creatine into sarcosine and urea is disclosed. The sarcosine and urea can then be determined in conventional manner. A reagent combination is provided which includes a creatinine standard, picric acid, an aqueous solution of NaOH, and creatinine amidohydrolase alone or together with buffer and optionally in admixture with creatinase, in an unmixed state before use. Another reagent combination has a buffer, reduced nicotinamide-adeninedinucleotide (NADH), adenosine triphosphate (ATP) and phosphoenolpyruvate (PEP); lactate dehydrogenase (LDH), pyruvate kinase (PK) and magnesium chloride; (3) creatine kinase and (4) creatinine amidohydrolase.

Notwithstanding these efforts by prior workers in the field, there has remained the difficulty that the reagents necessary have not been compatible in a single aqueous solution. Further, tests have required caustic reagents, such as strong acids or bases. Thus it has heretofore been impossible to provide a unitized test composition or to incorporate the test reagents in a conveniently used format.

Also, prior tests have been designed for reading of ultraviolet light absorbance, thus requiring time consuming procedures and expensive equipment.

OBJECTS OF THE INVENTION

It is therefore a principal object of the present invention to provide an improved test for determination of creatinine and enzymatic products thereof.

It is another object of the present invention to provide creatinine test means, such as a composition or device, which is particularly suitable for convenient testing of body fluid samples.

Still another object of the present invention is to provide a creatinine test which can be interpreted visually.

A further object of the present invention is to provide a creatinine test which is substantially free of caustic reagents.

It is another object of the present invention to provide a creatinine test wherein the above-mentioned advantages are provided by a composition comprising a creatinine hydrolyzing enzyme, creatine amidinohydrolase, sarcosine dehydrogenase and a tetrazolium indicator.

Other objects and a fuller understanding of the invention will be had by referring to the following description and claims drawn to preferred embodiments thereof.

SUMMARY OF THE INVENTION

In accordance with the present invention there are provided test means such as a composition or device, a method of making the test device, and a process for determination of creatinine and enzymatic products thereof. More particularly, creatinine is measured by contacting a fluid sample to be tested with test means, such as a composition comprising a creatinine hydrolyzing enzyme, creatine amidinohydrolase, sarcosine dehydrogenase and a tetrazolium indicator, and observing any resultant color change. A colored formazan is produced in proportion to the creatinine present. The sensitivity of the system is increased and the detection limit lowered by including formaldehyde dehydrogenase, diaphorase and nicotinamide adenine dinucleotide (NAD). Creatine or sarcosine are measured in this system by deletion of the creatinine hydrolyzing enzyme or the creatinine hydrolyzing enzyme and the creatine amidinohydrolase, respectively. The enzymes, tetrazolium dye and other components are compatible and may be combined in a single solution. The compositions are advantageously incorporated with a carrier, such as a matrix or tablet, to provide a test device.

In a preferred embodiment the tetrazolium indicator used is 3-(4,5-dimethyl-2-thiazolyl)-2,5-diphenyl-2H-tetrazolium bromide [thiazolyl blue, MTT]. Other tetrazolium dyes which, likewise, are used include 2-p-iodophenyl-3-p-nitrophenyl-5-phenyl-2H-tetrazolium chloride [INT], 3,3'-(3,3'-dimethoxy-4, 4'-biphenylene)-bis-(2-p-nitrophenyl-5-phenyl-2H-tetrazolium chloride) [nitroblue tetrazolium, NBT] and 3,3'-dimethoxy-4,4'-biphenylene) -bis-(2,5-p-nitro-phenyl-2H-tetrazolium chloride [tetranitroblue tetrazolium, TNBT].

Among the creatinine hydrolying enzymes which are useful in the present invention, creatinine amidohydrolase is especially preferred.

In another embodiment, used for the detection of creatine rather than creatinine, the composition essentially comprises creatine amidinohydrolase, sarcosine dehydrogenase and a tetrazolium indicator. Here also, the preferred indicator is thiazolyl blue.

The heretofore unrecognized properties and advantages of the present invention are believed to result through a mechanism described below, although this is not a theory on which the invention must be based.

The measurement of creatinine is accomplished by determining the product produced when the creatinine hydrolyzing enzyme catalyzes the hydrolysis of creatinine to creatine, as described in reaction (1).

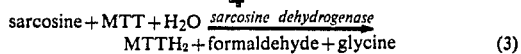

creatinine + H$_2$O $\xrightarrow{\text{creatinine hydrolyzing enzyme}}$ creatine     (1)

The creatine thus produced is determined by use of creatine amidinohydrolase, sarcosine dehydrogenase and the tetrazolium indicator, for example, thiazolyl blue (MTT), as in reactions (2)—(3).

creatine + H$_2$O $\xrightarrow{\text{creatine amidinohydrolase}}$ sarcosine + urea     (2)

In reaction (2), the creatine amidinohydrolase catalyzes the hydrolysis of creatine to sarcosine and urea. This is followed by the oxidative demethylation of sarcosine to formaldehyde and glycine by sarcosine dehydrogenase in reaction (3). The MTT serves as a hydrogen acceptor in the latter reaction and is converted to the colored formazan in stoichiometric quantities. Thus, for each mole of creatinine hydrolyzed in reaction (1) one mole of MTTH$_2$ (reduced form of MTT) is produced in reaction (3).

sarcosine + MTT + H$_2$O $\xrightarrow{\text{sarcosine dehydrogenase}}$ MTTH$_2$ + formaldehyde + glycine     (3)

The three enzymes and the tetrazolium indicator are compatible and are contained in a single aqueous solution. After the addition of a sample containing the creatinine, the amount of color produced is measured. The amount of color developed at any given time is proportional to the creatinine concentration, and thus an end point and rate assay are provided.

DESCRIPTION OF THE PREFERRED EMBODIMENTS

Figure 1:
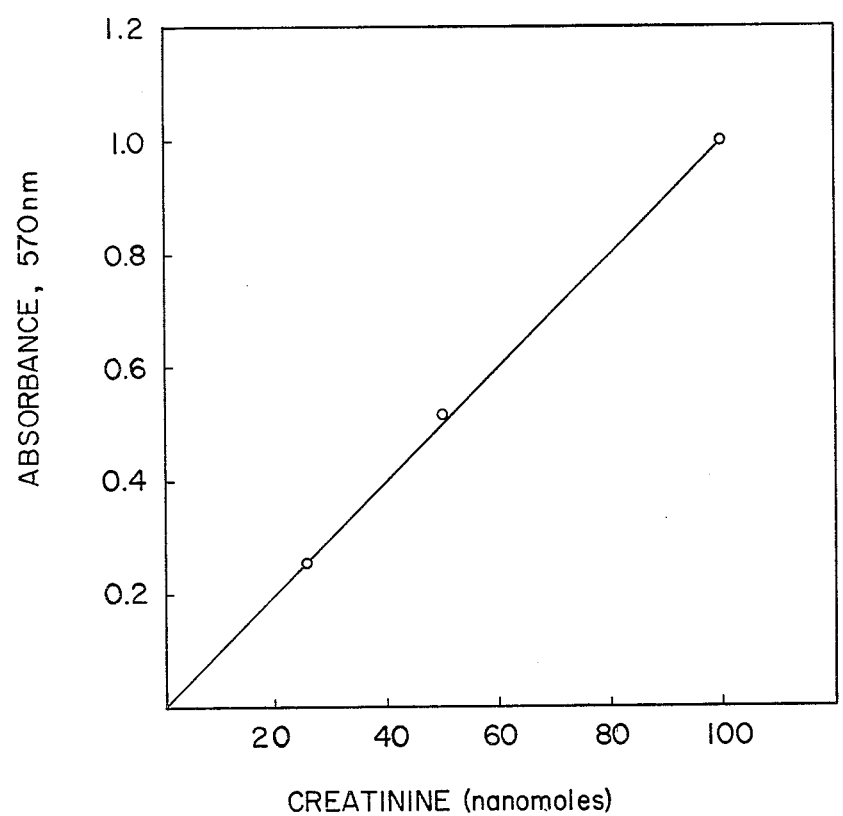
FIG. 1 is a graphical representation of the data reported in Example I for a creatinine test composition according to the invention, obtained by plotting absorbance vs. creatinine concentration.

Although specific terms are used in the following description for the sake of clarity, these terms are intended to refer only to the particular embodiments of the invention selected for exemplary illustration, and are not intended to define or limit the scope of the invention.

As set forth in one preferred embodiment, the composition of the present invention comprises creatinine amidinohydrolase, creatine amidinohydrolase, sarcosine dehydrogenase and thiazolyl blue. Sensitivity can be enhanced by further including formaldehyde dehydrogenase, diaphorase, and nicotinamide adenine dinucleotide (NAD).

The composition can further include stabilizing agents, carboxymethylcellulose and polyoxyethylene ethers of fatty alcohols (BRIJ ®) made by ICI United States, Inc., Wilmington, Del. 19897) being advantageously selected. These are present in total concentrations of at least about 0.5 milligrams/deciliter (mg/dl) aqueous solutions. Likewise surfactants or dispersants such as TRITON X—100 (Rohm & Haas Inc., Philadelphia, Pa.) can be used. A pH range of from about 7.5 to about 9 is preferred.

The activity of the enzyme preparation is measured by the number of units of activity per milligram of dry weight. The Commission on Enzymes of the International Union of Biochemistry has defined an International Unit (IU) of enzyme activity as 1 micromole ($\mu$mol) of substrate utilized per minute under specified conditions of pH and temperature control. The tetrazolium indicator and NAD are reported in millimolar (mM) concentrations.

A solution prepared of the composition can be made using physiological solutions, organic solvents or mixtures thereof. The preferred concentration range of the composition components is:

| | |
|---|---|
| creatinine hydrolyzing enzyme | 32–38 I.U./ml |
| creatine amidinohydrolase | 16–20 I.U./ml |
| sarcosine dehydrogenase | 1–2 I.U./ml |
| tetrazolium indicator and when used, | 1–2 mM |
| formaldehyde dehydrogenase | 1–4 I.U./ml |
| diaphorase | 1–5 I.U./ml |
| NAD | 4–6 mM |

The solution itself containing the compositions according to the invention may be used to detect body fluid constituents by adding it to a body fluid specimen such as urine, plasma or serum. Formation of the chromophoric complex with resultant color change is effected. However, the compositions according to the invention is advantageously used in the form of a solid preparation, rather than the solution itself.

Also provided are test devices incorporating the compositions of the invention and a method of making such reagent test devices which comprises contacting a carrier, such as a matrix or tablet, with the composition. When this contacting is by impregnation with a solution of the composition according to the invention, the carrier so contacted is then dried. In addition to impregnation, the devices of the present invention can be made by other suitable techniques such as printing or spraying the composition onto a substrate or matrix. The solvent used in preparing solutions for the method may be water, physiological solutions, organic solvents or mixtures thereof.

The concentration of reagents used in the impregnation solutions are in the following ranges:

| creatinine hydrolyzing enzyme | 320–380 I.U./ml |
| creatine amidinohydrolase | 80–90 I.U./ml |
| sarcosine dehydrogenase | 2–20 I.U./ml |
| tetrazolium indicator | 2–20 mM |
| and when used, | |
| formaldehyde dehydrogenase | 10–40 I.U./ml |
| diaphorase | 10–50 I.U./ml |
| NAD | 40–60 mM |

Solid preparations, as described below, are preferably incorporated with a carrier matrix in strip format. The term carrier matrix is envisioned to refer to bibulous and non-bibulous matrices which are insoluble in and maintain their structural integrity when exposed to water or physiological fluids. Suitable bibulous matrices which can be used include paper, cellulose, wood, synthetic resin fleeces, woven and nonwoven fabrics and the like. Non-bibulous matrices include organoplastic materials such as polystyrene, polypropylene or the like. When a bibulous matrix is employed, the matrix is advantageously affixed by suitable means, such as double-faced adhesive tape, to an insoluble support member, such as an organoplastic strip, for ease of use.

Alternatively, the compositions of the invention may be embodied in a carrier taking the form of a pressed or molded tablet containing conventional carrier material.

The test device is advantageously used by momentarily dipping it in a test sample or by otherwise introducing a test sample into the carrier matrix, whereby a detectable color change results when creatinine is present. Since characteristic color reaction takes place depending on the concentration of the creatinine, quantitative detection is possible. The test device may be used in the same way when samples of plasma, serum or other body fluids are tested.

The examples shown are merely illustrative and are not to be construed as a limitation of the invention. One skilled in the art will be able to make such variations, substitutions and changes in the ingredients and parameters as may seem desirable.

EXAMPLE I

A composition for determination of creatinine in a sample is prepared and used as described in this example.

The composition is prepared in solution according to the formulation of Table I.

TABLE I

| COMPOSITION FOR CREATININE DETERMINATION | |
| --- | --- |
| Creatinine hydrolyzing enzyme, 350 units/ml | 0.1 ml |
| Creatine amidinohydrolase, 90 units/ml | 0.2 ml |
| Sarcosine dehydrogenase, 2 units/ml | 0.5 ml |
| MTT, 10mM in 1% TRITON X-100 | 0.1 ml |
| Potassium phosphate, pH 7.5, 0.1M | 0.1 ml |

The above reagents were mixed together and preheated to 37° C. At this time the sample, containing from 10 to 100 nanomoles creatinine, is added and incubated at 37° C. for 60 minutes. After this time the absorbance of the solution is measured at 570 nanometers(nm). The absorbance of a reagent blank, consisting of all the reagents in the table minus the sample, is subtracted from the sample absorbance to give the true absorbance value. The value of the sample is determined by comparing the result to those of a series of creatinine standards having concentrations of 25, 50 and 100 nanomoles carried through the same procedure.

FIG. 1 illustrates the results obtained with this procedure. The results show the quantitative detection of creatinine.

EXAMPLE II

The sensitivity of the system illustrated in EXAMPLE I is increased and the detection limit lowered by changing the composition thereof to include:

| Formaldehyde dehydrogenase (30 IU/ml) | 0.1 ml |
| Diaphorase (30 IU/ml) | 0.1 ml |
| NAD (30mM) | 0.1 ml |

The reagents were added initially and the solution having the composition was prepared as in EXAMPLE I.

The overall reaction thus further includes reactions (4) and (5):

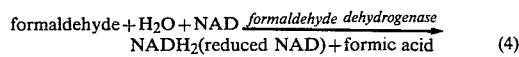

$$\text{formaldehyde} + H_2O + NAD \xrightarrow{\textit{formaldehyde dehydrogenase}} NADH_2(\text{reduced NAD}) + \text{formic acid} \quad (4)$$

$$NADH_2 + MTT \xrightarrow{\textit{diaphorase}} MTTH_2 + NAD \quad (5)$$

The oxidation of formaldehyde to formic acid in reaction (4) is catalyzed by the formaldehyde dehydrogenase with the simultaneous production of reduced NAD. This latter product is quantitated by the oxidized NAD in reaction (5). Thus, for each mole of creatinine hydrolyzed in reaction (1), two moles of $MTTH_2$ will be produced from the sum of reactions (2)–(5).

The system described in reactions (2)–(5) may also be used to measure creatine or sarcosine as well, by leaving out the first or first and second enzymes, respectively.

Although the invention has been described with a certain degree of particularity, it is understood that the present disclosure has been made only by way of example and that numerous changes may be resorted to without departing from the spirit and scope of the invention.

What is claimed is:

1. A composition for the detection of creatinine in a sample to be tested, which composition comprises a creatinine amidohydrolase, creatine amidinohydrolase, sarcosine dehydrogenase and a tetrazolium indicator.

2. The composition of claim 1 wherein the tetrazolium indicator is selected from thiazolyl blue, nitroblue tetrazolium, 2-p-iodophenyl-3-nitrophenyl-5-phenyl-2H-tetrazolium chloride and tetranitroblue tetrazolium.

3. The composition of claim 2 wherein the tetrazolium indicator is thiazolyl blue.

4. A solution comprising the composition of claim 1 and a buffer having a pH range of about 7.5 to about 9.

5. The composition of claim 1 which further comprises formaldehyde dehydrogenase, diaphorase, and nicotinamide adenine dinucleotide.

6. The composition of claim 2 which further comprises formaldehyde dehydeogenase, diaphorase, and nicotinamide adenine dinucleotide.

7. The composition of claim 3 which further comprises formaldehyde dehydrogenase, diaphorase, and nicotinamide adenine dinucleotide.

8. The composition of claim 5 wherein the tetrazolium dye is selected from the group of thiazolyl blue, nitroblue tetrazolium, 2-p-iodophenyl-3-nitrophenyl-5-phenyl-2H-tetrazolium chloride and tetranitrolblue tetrazolium.

9. A test device for determination of creatinine in a sample, which device comprises a carrier and, incorporated therewith, the composition of any of claims 2, 3 or 4.

10. A test device for the determination of creatinine in a sample which device comprises an inert carrier and, incorporated therewith, the composition of claim 5.

11. A method for preparing a creatinine detection device which comprises contacting a carrier with a solution comprising the composition of claim 1 and drying the carrier so contacted.

12. A method for preparing a creatinine detection device which comprises contacting a carrier with a solution comprising the composition of claim 5 and drying the carrier so contacted.

13. A method for determination of creatinine in a sample, which method comprises:
contacting the sample with the device of claim 9, and observing any color produced.

14. A method for determination of creatinine in a sample, which method comprises:
contacting the sample with the device of claim 9, and observing any color produced.

15. The method of claim 13 wherein the observation is done spectrophotometrically.

16. The method of claim 14 wherein the observation is done spectrophotometrically.

17. A composition for the detection of creatine in a sample to be tested which composition comprises creatine amidinohydrolase, sarcosine dehydrogenase, and a tetrazolium indicator.

18. The composition of claim 17 wherein the indicator is selected from thiazolyl blue, nitroblue tetrazolium, 2-p-iodophenyl-3-p-nitrophenyl-5-phenyl-2H-tetrazolium chloride and tetranitroblue tetrazolium.

19. The composition of claim 17 which further comprises a buffer having a pH of from about 7.5 to about 9.

20. The composition of claim 17 which further comprises formaldehyde dehydrogenase, diaphorase, and nicotinamide adenine dinucleotide.

21. A creatine detection device which comprises a carrier matrix incorporated with the composition of claim 17 in an amount sufficient to detectably react with creatine in the sample to be tested.

22. A creatine detection device which comprises a carrier matrix incorporated with the composition of claim 20 in an amount sufficient to detectably react with creatine in the sample to be tested.

23. The device of claim 21 wherein the carrier matrix is a bibulous or non-bibulous strip.

24. The device of claim 22 wherein the carrier matrix is a bibulous or non-bibulous strip.

25. A method for preparing a creatine detection device which comprises contacting a carrier matrix with a solution comprising the composition of claim 17 and drying the matrix so contacted.

26. A method for preparing a creatine detection device which comprises contacting a carrier matrix with a solution comprising the composition of claim 20 and drying the matrix so contacted.

27. A method for quantitative and qualitative determination of creatine in a sample to be tested which comprises:
contacting the sample with the device of claim 23, and measuring the amount of color produced.

28. The method of claim 27 wherein the measuring is done spectrophotometrically.

* * * * *